United States Patent
Yokouchi et al.

(10) Patent No.: US 10,542,866 B2
(45) Date of Patent: Jan. 28, 2020

(54) MEDICAL IMAGING DEVICE

(71) Applicant: Sony Olympus Medical Solutions Inc., Tokyo (JP)

(72) Inventors: Masahito Yokouchi, Tokyo (JP); Yuichi Yamada, Tokyo (JP)

(73) Assignee: SONY OLYMPUS MEDICAL SOLUTIONS INC., Tokyo (JP)

( * ) Notice: Subject to any disclaimer, the term of this patent is extended or adjusted under 35 U.S.C. 154(b) by 0 days.

(21) Appl. No.: 16/164,095

(22) Filed: Oct. 18, 2018

(65) Prior Publication Data

US 2019/0167071 A1 Jun. 6, 2019

(30) Foreign Application Priority Data

Dec. 1, 2017 (JP) .................. 2017-232158

(51) Int. Cl.
*A61B 1/00* (2006.01)
*A61B 1/06* (2006.01)
*A61B 1/04* (2006.01)

(52) U.S. Cl.
CPC ...... *A61B 1/00009* (2013.01); *A61B 1/00006* (2013.01); *A61B 1/00193* (2013.01); *A61B 1/0661* (2013.01); *A61B 1/00142* (2013.01); *A61B 1/04* (2013.01)

(58) Field of Classification Search
None
See application file for complete search history.

(56) References Cited

U.S. PATENT DOCUMENTS

2015/0054929 A1* 2/2015 Ito .................. A61B 1/273
 348/65
2019/0174029 A1* 6/2019 Mandai .................. G06T 7/11

FOREIGN PATENT DOCUMENTS

JP 2013197652 A * 9/2013
WO WO 2013/031512 A1 3/2013

* cited by examiner

*Primary Examiner* — Janese Duley
(74) *Attorney, Agent, or Firm* — Xsensus LLP (57) ABSTRACT

A medical imaging device includes: a first and a second imaging units configured to capture a first and a second optical images having parallax, respectively; a first and a second imaging optical systems configured to form the first and the second optical images on light receiving surfaces of the first and the second imaging units, respectively; a dirt detecting unit configured to detect dirt adhered to at least one of the first and the second imaging optical systems; an image generation unit configured to generate a three-dimensional image based on a first captured image based on the first image signal and a second captured image based on the second image signal; and an image selector configured to select a captured image to be output from the first captured image and the second captured image based on a detection result of the dirt by the dirt detecting unit.

18 Claims, 7 Drawing Sheets

MEDICAL IMAGING DEVICE

CROSS-REFERENCE TO RELATED APPLICATION

The present application claims priority to and incorporates by reference the entire contents of Japanese Patent Application No. 2017-232158 filed in Japan on Dec. 1, 2017.

BACKGROUND

The present disclosure relates to a medical imaging device.

In medical endoscope systems, the demand for observation by stereoscopic viewing is increasing. In the related art, various systems are known as endoscope systems for stereoscopic viewing. For example, WO 2013/031512 A discloses an endoscope system for stereoscopic viewing including a rigid endoscope (endoscope) having a left-eye optical system and a right-eye optical system and two imaging units for capturing a left-eye image signal and a right-eye image signal, respectively, based on light collected by the respective optical systems.

SUMMARY

In such an endoscope system, a user such as a surgeon records a desired image by pressing a button at a timing when an image to be desired to be recorded is displayed. At this time, in accordance with an instruction from the user, a moving image or a still image is recorded. In the recording of the image, an image signal of a preset one (for example, a left-eye image signal) out of the left-eye image signal and the right-eye image signal described above is output to the recording medium as data for recording.

However, even in a case where dirt adheres to the optical system to be recorded and the dirt is reflected in the image signal for recording, in some cases, the image signal may be recorded. Since the user observes a stereoscopic image (three-dimensional image) generated based on a left-eye image signal and a right-eye image signal, it is difficult for the user to notice that dirt is reflected only to one of the left-eye image signal and the right-eye image signal, and it is hard for the user to notice that the image signal in which the dirt is reflected is recorded. In many cases, the image signal recorded on the recording medium is often displayed on a monitor or the like after the observation by the endoscope is finished, and thus, after the observation, the user notices that the image signal in which the dirt is reflected is recorded. For this reason, there has been a demand for a technique capable of recording an image signal suitable for recording, that is, an image signal in which the dirt affecting the observation is not reflected during the observation by the endoscope.

There is a need for a medical imaging device that is able to record an appropriate image signal at the time of recording one of image signals for stereoscopic viewing.

A medical imaging device according to one aspect of the present disclosure includes: a first imaging unit configured to capture a first optical image having parallax; a second imaging unit configured to capture a second optical image having parallax; a first imaging optical system configured to form the first optical image on a light receiving surface of the first imaging unit; a second imaging optical system configured to form the second optical image on a light receiving surface of the second imaging unit; a dirt detecting unit configured to detect dirt adhered to at least one of the first and the second imaging optical systems by using at least one of a first image signal captured by the first imaging unit and a second image signal captured by the second imaging unit; an image generation unit configured to generate a three-dimensional image based on a first captured image based on the first image signal and a second captured image based on the second image signal and cause a display device to display one of the first captured image, the second captured image, and the three-dimensional image; and an image selector configured to select a captured image to be output to an outside from the first captured image and the second captured image based on a detection result of the dirt by the dirt detecting unit.

DETAILED DESCRIPTION

Hereinafter, embodiments will be described. In the embodiments, as an example of a medical imaging device according to the present disclosure, a medical endoscope apparatus for capturing and displaying an image inside a subject such as a patient will be described. In addition, the present disclosure is not limited by these embodiments. Furthermore, in the description of the drawings, the same components are denoted by the same reference numerals.

First Embodiment

Figure 1:
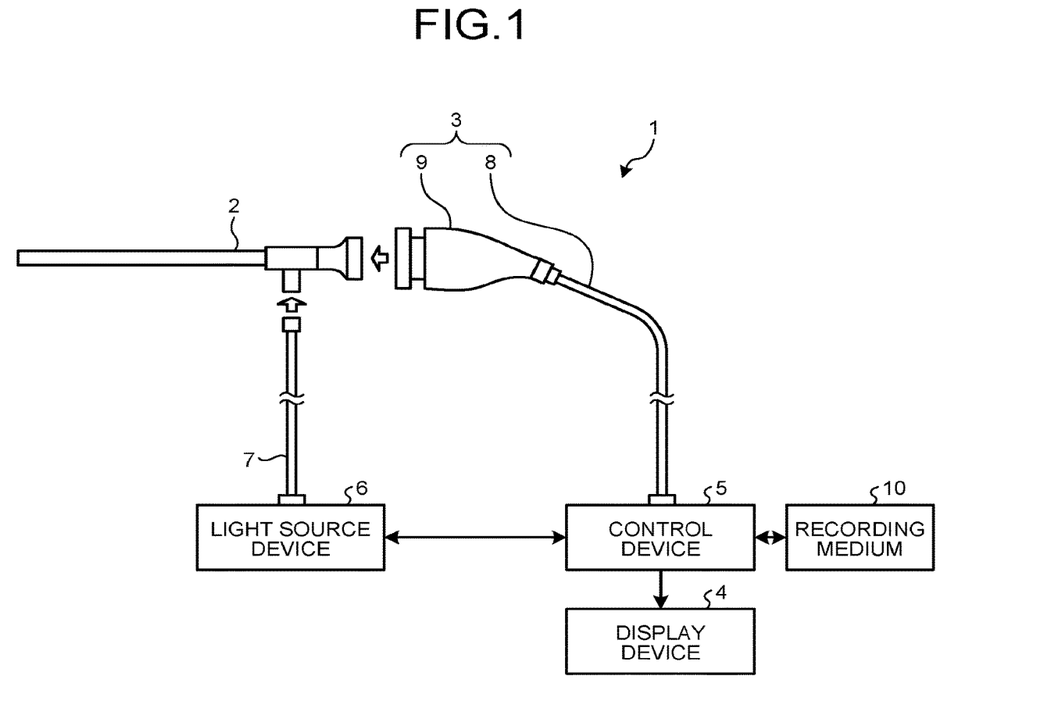
FIG. 1 is a diagram illustrating a schematic configuration of an endoscope apparatus according to a first embodiment.

FIG. 1 is a diagram illustrating a schematic configuration of an endoscope apparatus 1 according to a first embodiment. The endoscope apparatus 1 is a device which is used in a medical field and observes a subject of an inner portion (in vivo) of an observation object such as a person. As illustrated in FIG. 1, the endoscope apparatus 1 includes an endoscope 2, an imaging device 3 (medical imaging device), a display device 4, a control device 5, and a light source device 6. A medical image acquisition system is configured with the imaging device 3 and the control device 5. In addition, in the first embodiment, the endoscope apparatus using a rigid endoscope is configured with the endoscope 2 and the imaging device 3.

The endoscope 2 has a rigid elongated shape and is inserted into a living body. Inside the endoscope 2, an optical system configured by using one or a plurality of lenses to collect a subject image is provided. The endoscope 2 emits the light supplied through a light guide 7 from the distal end and irradiates the inside of the living body with the light. Then, the light (subject image) with which the inside of the living body is irradiated is collected by the optical system (a left-eye lens unit 91 and a right-eye lens unit 93 to be described later) inside the endoscope 2.

The imaging device 3 captures a subject image from the endoscope 2 and outputs the imaging result. As illustrated in FIG. 1, the imaging device 3 includes a transmission cable 8 as a signal transmission unit and a camera head 9. In the first embodiment, the transmission cable 8 and the camera head 9 constitute a medical imaging device.

The camera head 9 is detachably connected to a proximal end of the endoscope 2. Then, under the control of the control device 5, the camera head 9 captures the subject image collected by the endoscope 2 and outputs an imaging signal obtained by the capturing. In addition, the detailed configuration of the camera head 9 will be described later.

One end of the transmission cable 8 is detachably connected to the control device 5 via a connector, and the other end thereof is also detachably connected to the camera head 9 via a connector. Specifically, the transmission cable 8 is a cable in which a plurality of electric wires (not illustrated) is arranged inside the outer sheath which is the outermost layer. The plurality of electric wires is electric wires for transmitting the imaging signals output from the camera head 9, the control signals output from the control device 5, synchronization signals, clocks, and power to the camera head 9.

Under the control of the control device 5, the display device 4 displays the image generated by the control device 5. In order to easily obtain immersive feeling at the time of observation, it is preferable that the display device 4 has a display unit of 55 inches or more, but the present disclosure is not limited thereto.

The control device 5 processes the imaging signal input from the camera head 9 via the transmission cable 8, outputs the image signal to the display device 4, and overall controls the operations of the camera head 9 and the display device 4. In addition, the detailed configuration of the control device 5 will be described later.

One end of the light guide 7 is connected to the endoscope 2, and the light source device 6, supplies white illumination light for illuminating the inside of the living body to the one end of the light guide 7. One end of the light guide 7 is detachably connected to the light source device 6, and the other end thereof is also detachably connected to the endoscope 2. The light guide 7 transmits the light supplied from the light source device 6 from the one end to the other end to supply the light to the endoscope 2.

In addition, a recording medium 10 is connected to the control device 5. The recording medium 10 is configured with a device that is detachable from the control device 5 such as a recorder and a USB memory. In addition, communication between the control device 5 and the recording medium 10 is applicable as long as the communication such as a serial digital interface (SDI), a display port, or a high-definition multimedia interface (HDMI) is capable of inputting and outputting images. In addition, the memory (not illustrated) provided inside the control device 5 may be used as the recording medium 10.

Figure 2:
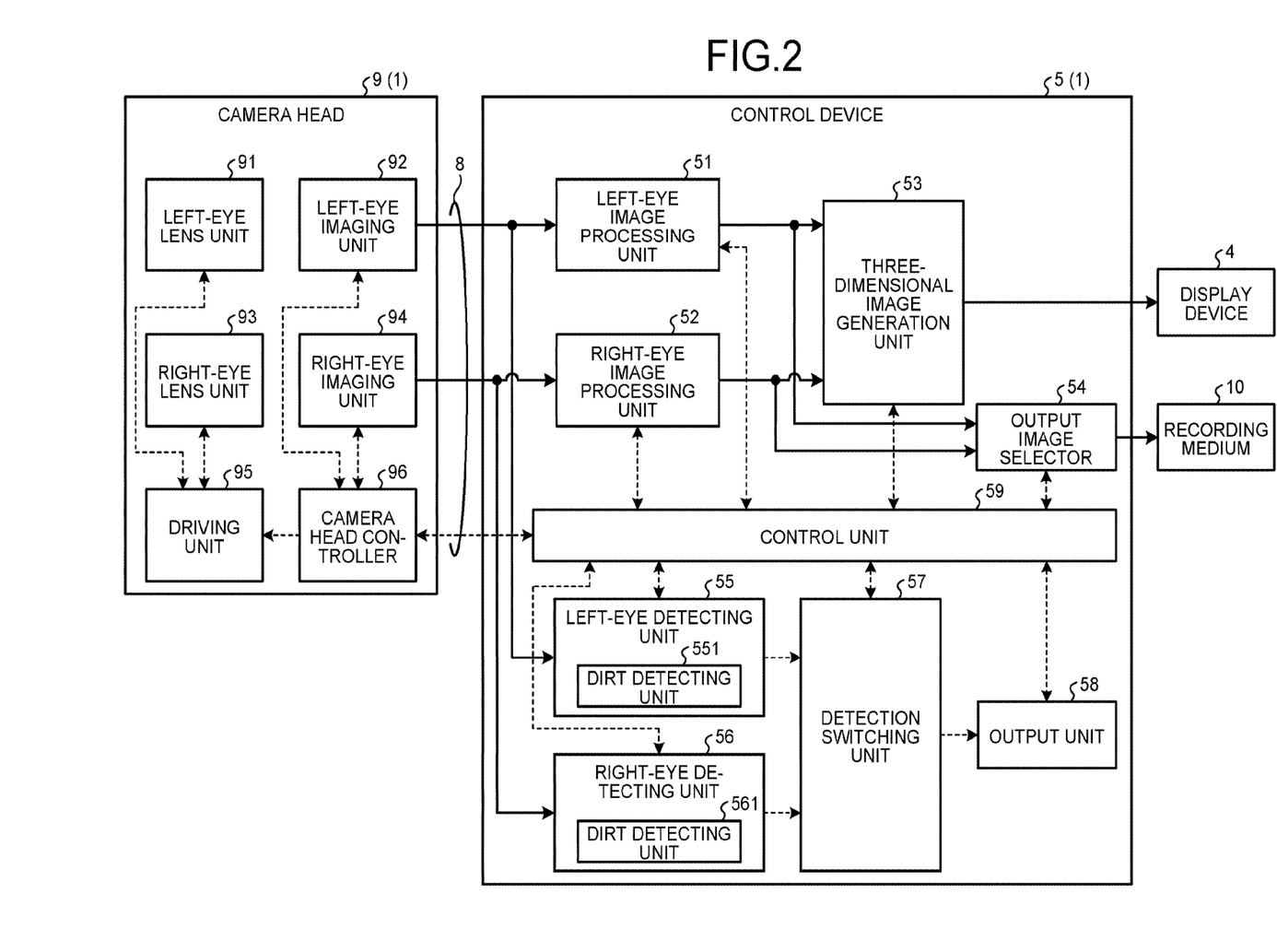
FIG. 2 is a block diagram illustrating configurations of a camera head and a control device illustrated in FIG. 1.

Next, the configuration of the imaging device 3 and the control device 5 will be described. FIG. 2 is a block diagram illustrating the configuration of the camera head 9 and the control device 5. In addition, in FIG. 2, transmission of signals related to an image is indicated by solid lines, and transmission of signals such as a control signal other than an image signal and light propagation paths are indicated by broken lines.

Hereinafter, the configuration of the camera head 9 and the configuration of the control device 5 will be described in this order. In addition, hereinafter, main components will be mainly described as the configurations of the control device 5 and the camera head 9. As illustrated in FIG. 2, the camera head 9 includes a left-eye lens unit 91 (imaging optical system), a left-eye imaging unit 92, a right-eye lens unit 93 (imaging optical system), a right-eye imaging unit 94, a driving unit 95, and a camera head controller 96.

The left-eye lens unit 91 is configured by using one or a plurality of lenses to collect incident observation light and forms a subject image on the imaging surface of an imaging element constituting the left-eye imaging unit 92. The one or the plurality of lenses is configured so as to be movable along an optical axis. In addition, the left-eye lens unit 91 is provided with an optical zoom mechanism (not illustrated) for changing an angle of view by moving the one or the plurality of lenses and a focus mechanism for changing a focal position under the control of the camera head controller 96. In addition, the left-eye lens unit 91 may be provided with an optical filter (for example, a filter that cuts off infrared light) that can be inserted and removed along the optical axis in addition to the optical zoom mechanism and the focus mechanism.

The left-eye imaging unit 92 captures an image of the subject under the control of the camera head controller 96. The left-eye imaging unit 92 is configured by using an imaging element that receives the subject image formed by the left-eye lens unit 91 and converts the subject image into an electric signal. The imaging element is configured with a charge coupled device (CCD) image sensor or a complementary metal oxide semiconductor (CMOS) image sensor. In a case where the imaging element is a CCD, for example, a signal processing unit (not illustrated) that performs signal processing (A/D conversion or the like) on an electric signal (analog signal) from the imaging element and outputs an imaging signal is mounted on a sensor chip or the like. In a case where the imaging element is a CMOS, for example, a signal processing unit that performs signal processing (A/D conversion or the like) on an electric signal (analog) obtained by converting light into the electric signal and outputs an imaging signal is included in the imaging element. The left-eye imaging unit 92 outputs the generated electric signal to the control device (a left-eye image processing unit 51).

The right-eye lens unit 93 is configured by using one or a plurality of lenses to collect incident observation light and forms a subject image on an imaging surface of an imaging element constituting the right-eye imaging unit 94. The one or the plurality of lenses is configured so as to be movable along an optical axis. In addition, the right-eye lens unit 93 is provided with an optical zoom mechanism (not illustrated) for changing an angle of view by moving the one or the plurality of lenses and a focus mechanism for changing a focal position under the control of the camera head controller 96. In addition, the right-eye lens unit 93 may be provided with an optical filter (for example, a filter that cuts off infrared light) that can be inserted and removed along the optical axis in addition to the optical zoom mechanism and the focus mechanism.

The right-eye imaging unit 94 captures an image of the subject under the control of the camera head controller 96. The right-eye imaging unit 94 is configured by using an imaging element that receives the subject image formed by the right-eye lens unit 93 and converts the subject image into an electric signal. The imaging element is configured with a CCD image sensor or a CMOS image sensor. The right-eye imaging unit 94 outputs the generated electric signal to the control device 5 (a right-eye image processing unit 5 2).

The driving unit 95 has a driver for operating the optical zoom mechanism and the focus mechanism under the control of the camera head controller 96 to change the angle of view and the focal position of the left-eye lens unit 91 and the right-eye lens unit 93.

The camera head controller 96 controls the operation of the entire camera head 9 in accordance with a drive signal input via the transmission cable 8, an instruction signal output from an operating unit by a user's operation on the operating unit such as a switch exposed on the outer surface of the camera head 9, and the like. In addition, the camera head controller 96 outputs information on a current state of the camera head 9 to the control device 5 via the transmission cable 8.

Incidentally, the driving unit 95 and the camera head controller 96 described above are realized by using a general-purpose processor such as a central processing unit (CPU) having an internal memory (not illustrated) in which a program is recorded or a dedicated processor such as various arithmetic circuits for executing functions such as an application specific integrated circuit (ASIC). In addition, the driver and the camera head controller may be configured by using a field programmable gate array (FPGA) which is one type of a programmable integrated circuit. Incidentally, in a case where the driver and the camera head controller are configured by using the FPGA, a memory for storing a configuration data may be provided, and the FPGA as the programmable integrated circuit may be configured from the configuration data read from the memory.

In addition, a signal processing unit for performing signal processing on the electric signals generated by the left-eye imaging unit 92 and the right-eye imaging unit 94 may be configured in the camera head 9 and the transmission cable 8. In addition, the signal processing unit may be allowed to generate an imaging clock for driving the left-eye imaging unit 92 and the right-eye imaging unit 94 and a driving clock for driving the driving unit 95 based on a reference clock generated by an oscillator (not illustrated) provided inside the camera head 9 and to output the imaging clock and the driving clock to the left-eye imaging unit 92, the right-eye imaging unit 94 and the driving unit 95, respectively. Alternatively, the signal processing unit may be allowed to generate timing signals for various processes in the left-eye imaging unit 92, the right-eye imaging unit 94, the driving unit 95, and the camera head controller 96 based on a synchronization signal input from the control device 5 via the transmission cable 8 and to output the timing signals to the left-eye imaging unit 92, the right-eye imaging unit 94, the driving unit 95 and the camera head controller 96, respectively. In addition, the camera head controller 96 may be provided in the transmission cable 8 or the control device 5 instead of the camera head 9.

As illustrated in FIG. 2, the control device 5 includes a left-eye image processing unit 51, a right-eye image processing unit 52, a three-dimensional image generation unit 53, an output image selector 54, a left-eye detecting unit 55, a right-eye detecting unit 56, a detection switching unit 57, an output unit 58, and a control unit 59. In addition, a power supply unit (not illustrated) that generates a power supply voltage for driving the control device 5 and the camera head 9, supplies the power supply voltage to each component of the control device 5, and supplies the power supply voltage to the camera head 9 via the transmission cable 8 and the like may be provided to the control device 5.

The left-eye image processing unit 51 outputs, to the three-dimensional image generation unit 53, a left-eye image signal generated by performing image processing such as a synchronization process, a white balance (WB) adjustment process, a gain adjustment process, a gamma correction process, a digital/analog (D/A) conversion process, and a format conversion process on the electric signal output by the camera head 9 (the left-eye imaging unit 92).

The right-eye image processing unit 52 outputs, to the three-dimensional image generation unit 53, a right-eye image signal generated by performing the same image processing as that of the left-eye image processing unit 51 on the electric signal output by the camera head 9 (the right-eye imaging unit 94).

The three-dimensional image generation unit 53 generates a three-dimensional image signal corresponding to a display system of the display device 4 as a display image signal by using the left-eye image signal generated by the left-eye image processing unit 51 and the right-eye image signal generated by the right-eye image processing unit 52. As the image generated by the three-dimensional image generation unit 53, there may be exemplified an image corresponding to a line-by-line system or an image corresponding to a side-by-side system. The three-dimensional image generation unit 53 outputs the generated three-dimensional image signal to the display device 4. In addition, in a case where the display device 4 is set to display a two-dimensional image, an image signal for display corresponding to the display system of the display device 4 is generated and output by using the same image signal (the left-eye image signal or the right-eye image signal) as that of the output image selector 54.

Under the control of the control unit 59, the output image selector 54 selects, the image signal from the left-eye image signal generated by the left-eye image processing unit 51 and the right-eye image signal generated by the right-eye image processing unit 52 based on the dirt detection result and outputs the image signal to the recording medium 10 connected to the control device 5. When the preset condition is satisfied, for example, when an instruction to record an image is input by the user, or when a predetermined time has elapsed, the output image selector 54 outputs the selected image signal to the recording medium 10.

The left-eye detecting unit 55 performs a detection process on the electric signal output from the camera head (the left-eye imaging unit 92). The left-eye detecting unit 55 executes the detection process based on, for example, the image signal (Y, $C_D/C_R$ signal) obtained by processing the electric signal. Specifically, the left-eye detecting unit 55 executes, based on pixel information (a luminance signal (Y signal)) for each pixel in the predetermined region (hereinafter, referred to as a detection region) in the entire captured image of one frame captured by the left-eye imaging unit 92, detection of a contrast and a frequency component of the image in the detection region, detection of an average luminance value and maximum and minimum pixels in the detection region by a filter, or the like, comparison determination with a threshold value, detection of a histogram, and the like. Then, the left-eye detecting unit 55 outputs the detection information (the contrast, the frequency component, the luminance average value, the maximum and minimum pixels, the histogram, and the like) obtained by the detection to the detection switching unit 57. In addition, the detection information is output to the camera head controller 96 via the control unit 59, and in the camera head controller 96, the autofocus processing is executed.

Figure 3:
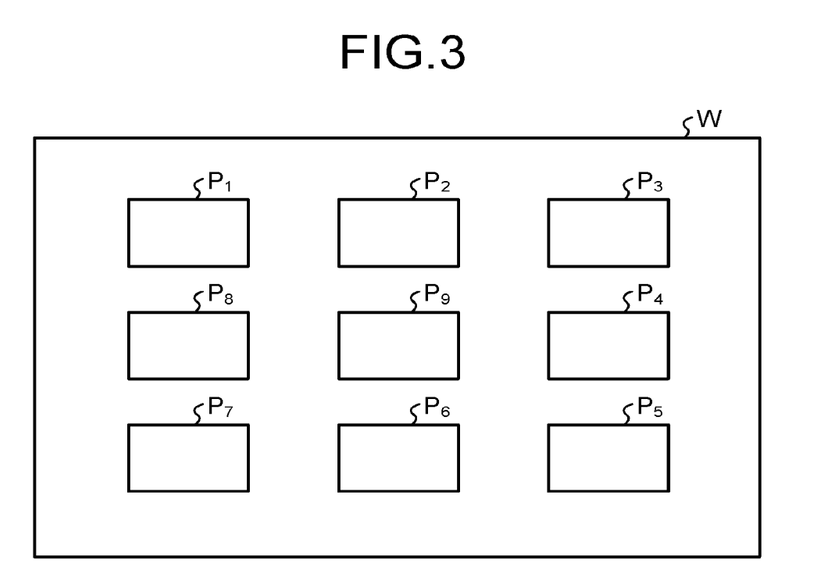
FIG. 3 is a diagram illustrating a dirt detection process in the control device according to the first embodiment.

In addition, the left-eye detecting unit 55 includes a dirt detecting unit 551. FIG. 3 is a diagram illustrating a dirt detection process in the control device 5 according to the first embodiment. For example, the dirt detecting unit 551 performs the dirt detection based on the contrast of the image detected by the detection process for a plurality of detection regions (nine detection regions $P_1$ to $P_9$ in FIG. 3) set in the image W illustrated in FIG. 3. For example, the dirt detecting unit 551 detects the focal position from the contrast of the image in the detection region $P_1$, and determines whether or not the focal position is on the surface of the objective lens of the endoscope 2. If the detected focal position is on the surface of the objective lens, the dirt detecting unit 551 determines that dirt adheres to the detection region. On the other hand, if the detected focal position is a position different from that on the surface of the objective lens, the dirt detecting unit 551 determines that no dirt adheres to the detection region. Similarly, the dirt detection is performed in the detection regions $P_2$ to $P_9$, and if the number of detection regions in which dirt is detected is equal to or larger than a preset number, it is determined that dirt adheres to the left-eye optical system. The dirt detecting unit 551 outputs the result of the dirt detection to the detection switching unit 57. Dirt here refers to body fluids such as blood and pancreatic juice and water droplets adhered to the lens.

In addition, the dirt detecting unit 551 may set the positions of the detection regions, the patterns of the detection regions, and the like in addition to the number of the detection regions where the dirt is detected and may detect, based on the positions and patterns of the detection regions where the dirt is detected, whether or not the dirt adheres.

In addition, the dirt detecting unit 551 may perform the dirt detection from an outer detection region of the image W toward an inner detection region in a spiral shape or may perform the dirt detection on a detection region located at the center of the image W, and after that, perform the dirt detection on a detection region located on the outer circumference of the detection region. Since an important observed region or the like is often located at the center of the image W, for example, by first performing the dirt detection on the detection region located at the center of the image W, the region in the useful observed region is reflected is preferentially processed.

In addition, the dirt detecting unit 551 may be configured so as to calculate a degree of dirt. The dirt detecting unit 551 may calculate a ratio of dirt on the lens surface of the optical system as a degree of dirt, for example, according to the number of detection regions where the dirt is detected or may set a weight for each detection region and calculate the degree of dirt based on the detection result obtained by adding the weight to the detection region in which the dirt is detected.

In addition, the detection region for auto focusing by the left-eye detecting unit 55 and the detection region for dirt detection by the dirt detecting unit 551 may be the same as or different from each other.

The right-eye detecting unit 56 performs a detection process on the electric signal output from the camera head (the right-eye imaging unit 94). Similarly to the left-eye detecting unit 55, the right-eye detecting unit 56 performs the detection process and outputs obtained detection information to the detection switching unit 57 and the control unit 59.

In addition, the right-eye detecting unit 56 includes a dirt detecting unit 561. Similarly to the dirt detecting unit 551, the dirt detecting unit 561 determines that dirt adheres to the right-eye optical system. The dirt detecting unit 561 outputs the result of the dirt detection to the detection switching unit 57.

The detection switching unit 57 switches the detecting units that perform the detection process. Based on the dirt detection result in the previous frame, the detection switching unit 57 selects the detecting unit that performs the detection process among the left-eye detecting unit 55 and the right-eye detecting unit 56 and causes the selected detecting unit to execute the detection process. At this time, the dirt detecting unit included in the selected detecting unit executes the dirt detection process. In the first embodiment, the detection switching unit 57 has a switching function of the dirt detecting unit.

The output unit 58 is realized by using a speaker, a printer, a display, or the like and outputs various types of information. Under the control of the control unit 59, the output unit 58 performs outputting alarm sound or displaying images. For example, in a case where the detecting unit is switched by the detection switching unit 57, under the control of the control unit 59, the output unit 58 performs outputting alarm sound or an operation of displaying an image indicating that the detecting unit is switched. The output unit 58 also functions as a notification unit for notifying that dirt adheres to the left-eye lens unit 91 and/or the right-eye lens unit 93.

The control unit 59 performs drive control of each component including the control device 5 and the camera head 9, input/output control of information for each component, and the like. The control unit 59 generates a control signal with reference to communication information data (for example, communication format information or the like) recorded in a memory (not illustrated) and transmits the generated control signal to the imaging device 3. In addition, the control unit 59 outputs a control signal to the camera head 9 via the transmission cable 8.

In addition, the control unit 59 generates synchronization signals and clocks of the imaging device 3 and the control device 5. A synchronization signal (for example, a synchronization signal for instructing an imaging timing of the camera head 9 or the like) and a clock (for example, a clock for serial communication) to the imaging device 3 are transmitted to the imaging device 3 through a line (not illustrated), and the imaging device 3 is driven based on the synchronization signal and the clock.

In addition, the control device 5 is realized by using a semiconductor memory such as a flash memory or a dynamic random access memory (DRAM) and has a memory (not illustrated) for recording communication information data (for example, communication format information and the like). In addition, various programs and the like executed by the control unit 59 may be recorded in this memory.

The left-eye image processing unit 51, the right-eye image processing unit 52, the three-dimensional image generation unit 53, the output image selector 54, the left-eye detecting unit 55, the right-eye detecting unit 56, the detection switching unit 57, and the control unit 59 described above are realized by using a general purpose processor such as a CPU having an internal memory (not illustrated) in which a program is recorded or a dedicated processor such as various arithmetic circuits for executing specific functions such as an ASIC. In addition, these units may be configured by using an FPGA which is one type of a programmable integrated circuit.

In addition, a user interface for receiving inputs of various operation signals related to the endoscope apparatus 1 including the control device 5 may be provided.

Figure 4:
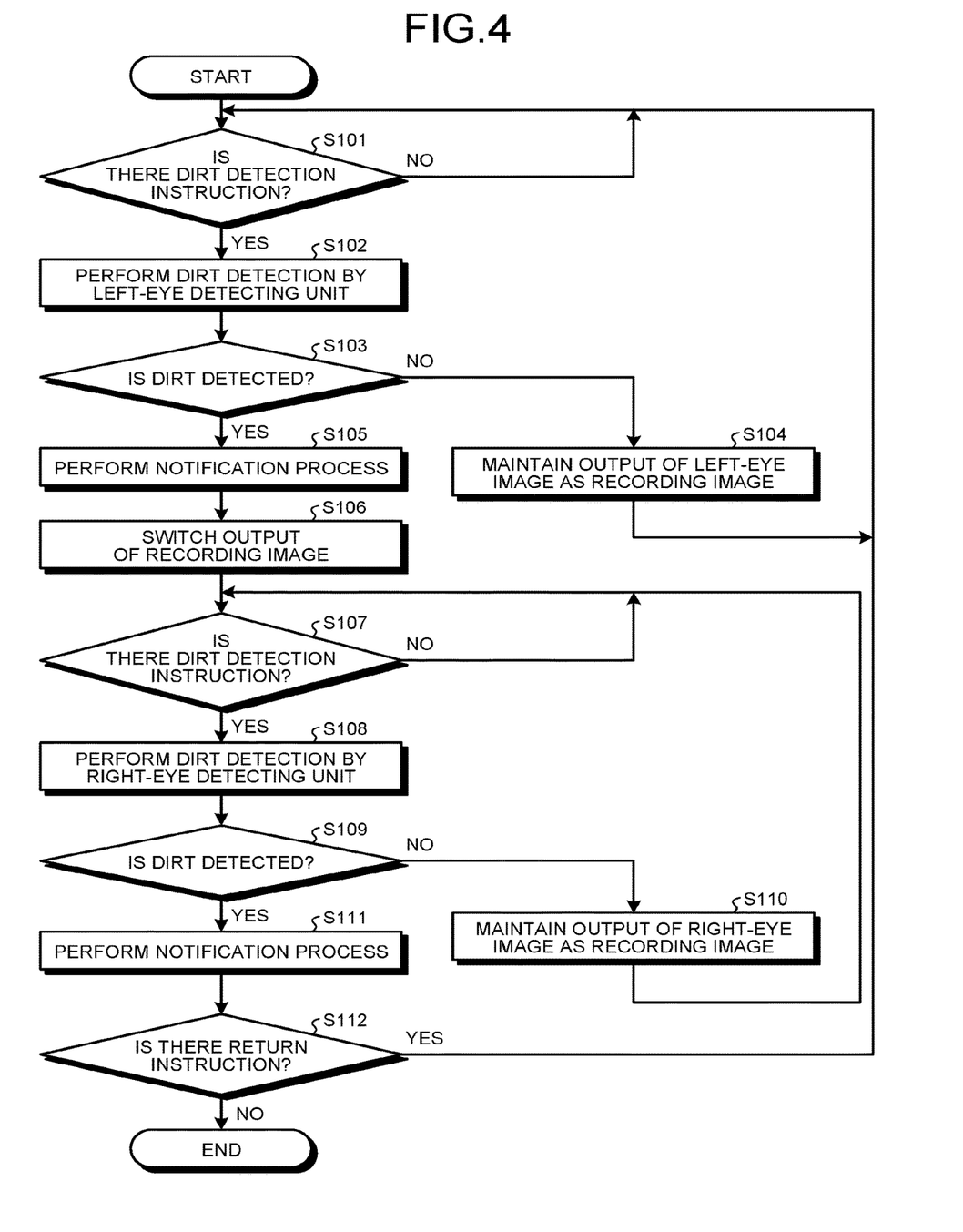
FIG. 4 is a flowchart illustrating processes performed by the endoscope apparatus according to the first embodiment.

Subsequently, the output switching operation of the image signal performed by the endoscope apparatus 1 will be described with reference to FIG. 4. FIG. 4 is a flowchart illustrating processes performed by the endoscope apparatus according to the first embodiment. Hereinafter, it is assumed that each unit operates under the control of the control unit 59. In addition, in the first embodiment, as an initial setting, the left-eye image signal is set to be output to the recording medium 10. At this time, the detecting unit that performs the detection process or the dirt detection process is set to the left-eye detecting unit 55.

The control unit 59 determines whether or not a dirt detection instruction is input (Step S101). Herein, the dirt detection instruction is input in a case where there is an input from the user or a preset condition is satisfied. As the preset condition, there may be exemplified such as a case where the setting of the dirt detection mode is turned on, a case where the power supply of the device is turned on, a case where the recording medium 10 is connected to the control device 5, or a case where recording start is detected by external communication.

In Step S101, in a case where the control unit 59 determines that there is a dirt detection instruction (Step S101: Yes), the process proceeds to Step S102. On the other hand, in a case where the control unit 59 determines that there is no dirt detection instruction (Step S101: No), the control unit 59 repeats checking the input of the instruction.

In Step S102, the left-eye detecting unit 55 performs a dirt detection process on the electric signal input from the camera head 9 (the left-eye imaging unit 92). Specifically, as described above, the dirt detecting unit 551 performs the dirt detection based on the contrast of the image detected by the detection process. The detection result by the dirt detecting unit 551 is output to the detection switching unit 57.

In Step S103 subsequent to Step S102, the detection switching unit 57 determines from the dirt detection result input from the left-eye detecting unit 55 whether or not dirt is detected. In a case where the detection switching unit 57 determines that no dirt is detected (Step S103: No), the process proceeds to Step S104.

In Step S104, the detection switching unit 57 maintains the detection process to be in the left-eye detecting unit 55 and maintains the image signal (recording image) to be output to the recording medium 10 to be in the left-eye image. For this reason, the output image selector 54 selects the left-eye image signal and outputs the left-eye image signal to the recording medium 10.

On the other hand, in a case where the detection switching unit 57 determines that dirt is detected (Step S103: Yes), the process proceeds to Step S105. In Step S105, the control unit 59 causes the output unit 58 to output a message that dirt is detected and the output image is switched. For example, the output unit 58 displays on the display the message that dirt is detected and the output image is switched or outputs an alarm sound indicating the message that dirt is detected and the output image is switched. In addition, this Step S105 may not be performed, and the process may proceed from Step S103 to Step S106.

In Step S106 subsequent to Step S105, the detection switching unit 57 switches the recording images to be output. Specifically, the detection switching unit 57 generates and outputs a control signal indicating a message that the right-eye image signal is selected as the image signal for output to the output image selector 54. As a result, the output image selector 54 selects the right-eye image signal and outputs the right-eye image signal to the recording medium 10.

In Step S107 subsequent to Step S106, the control unit 59 determines whether or not a dirt detection instruction is input. The dirt detection instruction in Step S107 is input in a case where there is an input from the user or a preset condition is satisfied. As the preset condition in Step S107, there may be exemplified such as the timing at which the detecting unit that performs the detection process is switched to the right-eye detecting unit 56 by the detection switching unit 57, or a case where a predetermined time has elapsed since the last dirt detection was performed.

In Step S107, in a case where the control unit 59 determines that there is a dirt detection instruction (Step S107: Yes), the process proceeds to Step S108. On the other hand, in a case where the control unit 59 determines that there is no dirt detection instruction (Step S107: No), the control unit 59 repeats checking the input of the instruction.

In Step S108, the right-eye detecting unit 56 performs a dirt detection process on the electric signal input from the camera head 9 (the right-eye imaging unit 94). Specifically, as described above, the dirt detecting unit 561 performs the dirt detection based on the contrast of the image detected by the detection process. The detection result by the dirt detecting unit 561 is output to the detection switching unit 57.

In Step S109 subsequent to Step S108, the detection switching unit 57 determines from the dirt detection result input from the right-eye detecting unit 56 whether or not dirt is detected. In a case where the detection switching unit 57 determines that no dirt is detected (Step S109: No), the process proceeds to Step S110.

In Step S110, the detection switching unit 57 maintains the detection process to be in the right-eye detecting unit 56 and maintains the image signal (recording image) to be output to the recording medium 10 to be in the right-eye image. For this reason, the output image selector 54 selects the right-eye image signal and outputs the right-eye image signal to the recording medium 10.

On the other hand, in a case where the detection switching unit 57 determines that dirt is detected (Step S109: Yes), the process proceeds to Step S111. In Step S111, the control unit 59 causes the output unit 58 to output a message that dirt adheres to both the left-eye lens unit 91 and the right-eye lens unit 93 and that there is a need to eliminate the dirt of the lens. For example, the output unit 58 displays on the display the message that there is a need to eliminate the dirt of the lens or outputs an alarm sound indicating the message that there is a need to eliminate the dirt of the lens.

In Step S112 subsequent to Step S111, the control unit 59 determines whether or not a return instruction is input. For example, in a case where a return operation is input from the user before a predetermined time has elapsed since the notification process in Step S111 was performed, the control unit 59 determines that the return instruction has been issued.

In Step S112, in a case where the control unit 59 determines that a return instruction is not input (Step S112: No), the process is ended. On the other hand, in a case where the control unit 59 determines that the return instruction is input (Step S112: Yes), the process returns to Step S101, and the above-described process is repeated. At this time, the detection switching unit 57 switches the detecting unit that performs the detection process to the left-eye detecting unit 55 and sets the output image selector 54 so as to select the left-eye image signal.

In addition, in Step S112 described above, the process may be automatically returned instead of a return instruction from the user. For example, in Step S112, in a case where the left-eye detecting unit 55 and the right-eye detecting unit 56 execute the dirt detection, and as a result of the detection by each detecting unit, in a case where no dirt is detected, the control unit 59 may assume that there is a return instruction and may cause the process to return to the output image Step S101 (Step S112: corresponding to Yes). At this time, the detection switching unit 57 switches the detecting unit that performs the detection process to the left-eye detecting unit 55 and sets the output image selector 54 to select the left-eye image signal. On the other hand, in a case where dirt is detected even if the dirt detection is performed within a preset number of times or a preset time, the control unit 59 may assume that there is no return instruction and may cause the process to be ended (Step S112: corresponding to No).

In the dirt detection process described above, for example, after the control device 5 is turned on and the first processing is executed, the dirt detection process is repeated at preset time intervals. As the time interval, for example, time (second), the number of frames, or the like may be exemplified.

In addition, in the dirt detection process described above, the example where the dirt detection process is performed first on the left-eye image signal and, if the dirt is detected, the dirt of the right-eye image signal is detected has been described. However, the dirt detection process may be performed first on the right-eye image signal.

In the first embodiment described above, the dirt detecting units (the dirt detecting units 551 and 561) are provided in the detecting units (the left-eye detecting unit 55 and the right-eye detecting unit 56), and in detecting the dirt, the detection switching unit 57 is allowed to switch the image signals (the left-eye image signal and the right-eye image signal) to be output to the recording medium 10. According to the first embodiment, at the time of recording one of the image signals for stereoscopic viewing, by suppressing the image in which the dirt is reflected from being recorded on the recording medium 10, it is possible to record an appropriate image signal.

Second Embodiment

Figure 5:
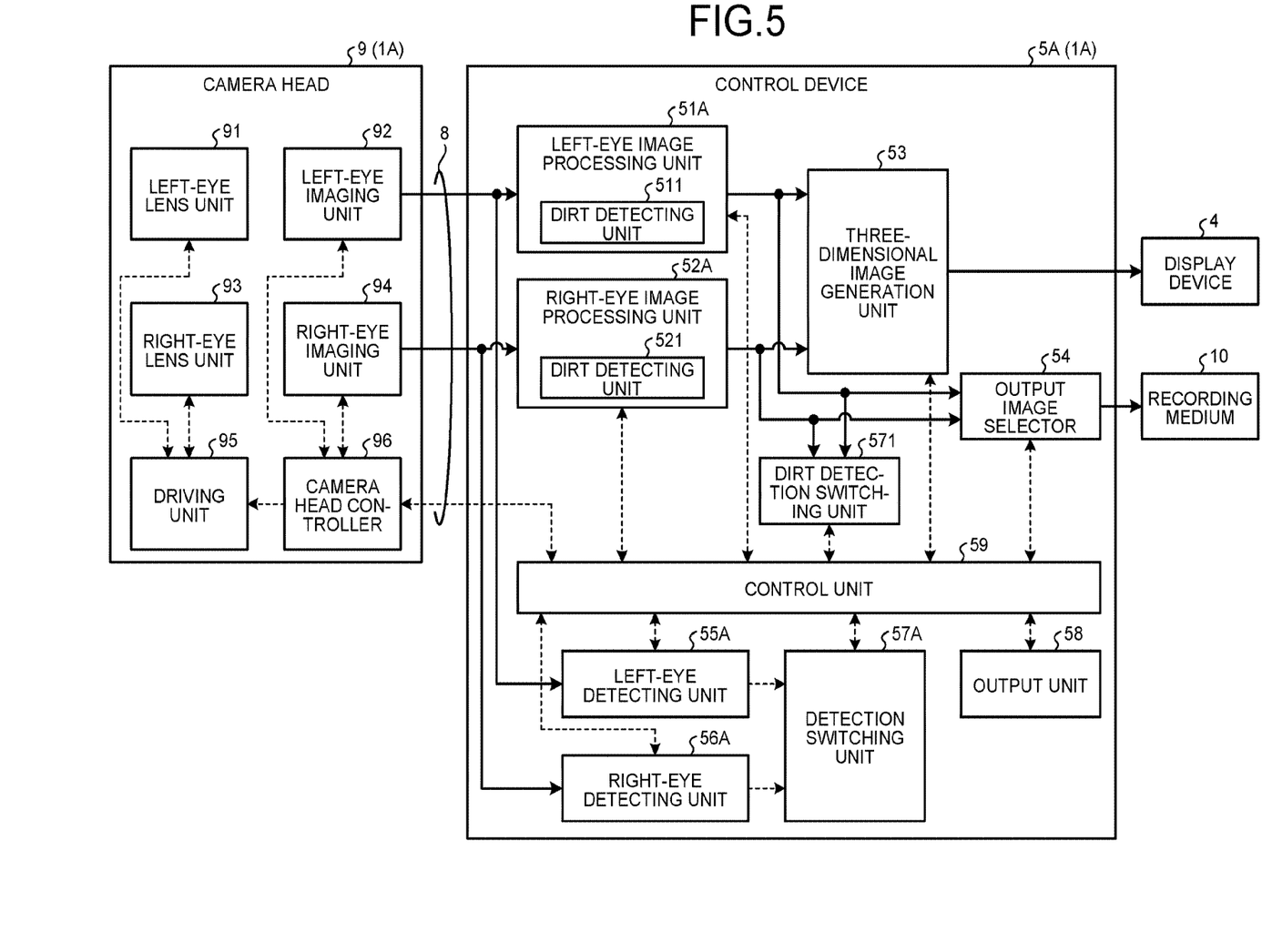
FIG. 5 is a block diagram illustrating configurations of a camera head and a control device included in an endoscope apparatus according to a second embodiment.

Next, a second embodiment will be described with reference to FIG. 5. FIG. 5 is a block diagram illustrating configurations of a camera head 9 and a control device 5A included in an endoscope apparatus 1A according to the second embodiment. In the above-described first embodiment, the dirt detecting unit is provided in the detecting unit. However, in the second embodiment, the dirt detecting unit is provided in the image processing unit.

The endoscope apparatus 1A according to the second embodiment includes the endoscope 2, the imaging device 3 (the camera head 9), the display device 4, and the light source device 6 described above (refer to FIG. 1 and the like), and the control device 5A. In the second embodiment, only configurations different from those of the above-described first embodiment will be described.

The control device 5A includes a left-eye image processing unit 51A, a right-eye image processing unit 52A, a three-dimensional image generation unit 53, an output image selector 54, a left-eye detecting unit 55A, a right-eye detecting unit 56A, a detection switching unit 57A, an output unit 58, a control unit 59, and a dirt detection switching unit 571.

The left-eye image processing unit 51A has the same functions as those of the above-described left-eye image processing unit 51 and includes a dirt detecting unit 511. Similarly to the dirt detecting unit 551, the dirt detecting unit 511 performs the detection process to detect dirt based on the contrast of the image detected by the detection process for the plurality of detection regions set in the left-eye image. The dirt detecting unit 511 outputs the result of the dirt detection to the control unit 59.

The right-eye image processing unit 52A has the same functions as those of the above-described right-eye image processing unit 52 and includes a dirt detecting unit 521. Similarly to the dirt detecting unit 561, the dirt detecting unit 521 performs the detection process to detect dirt based on the contrast of the image detected by the detection process for the plurality of the detection regions set in the right-eye image. The dirt detecting unit 521 outputs the result of the dirt detection to the control unit 59.

The left-eye detecting unit 55A performs a detection process on the electric signal output from the camera head (the left-eye imaging unit 92). As described above, the left-eye detecting unit 55A executes the detection process based on the image signal (Y, $C_B/C_R$ signal) obtained by processing the electric signal. The left-eye detecting unit 55A outputs the obtained detection information to the detection switching unit 57A. In the second embodiment, the left-eye detecting unit 55A does not perform the dirt detection process.

The right-eye detecting unit 56A performs a detection process on the electric signal output from the camera head (the right-eye imaging unit 94). Similarly to the left-eye detecting unit 55A, the right-eye detecting unit 56A executes the detection process and outputs the obtained detection information to the detection switching unit 57A. In the second embodiment, similarly to the left-eye detecting unit 55A, the right-eye detecting unit 56A does not perform the dirt detection process.

Based on the dirt detection result in the previous frame, the dirt detection switching unit 571 switches the detecting units that execute the dirt detection process from the dirt detecting units 511 and 521.

The detection switching unit 57A switches the detecting units that perform a detection process. Based on the dirt detection result in the previous frame, the detection switching unit 57 selects the detecting unit that performs the detection process among the left-eye detecting unit 55A and the right-eye detecting unit 56, and causes the selected detecting unit to execute the detection process.

The flow of processes relating to the selection of the detecting unit and the dirt detecting unit and the switching of the output image are the same as the flowchart illustrated in FIG. 4 described above. Each component executes the corresponding process, so that the processes similar to those of the first embodiment are executed. Specifically, when dirt is detected by the dirt detecting unit 511, under the control of the control unit 59, the detecting unit that executes the dirt detection process is switched to the dirt detecting unit 521, and the detecting unit and the image signal to be output are also switched.

In the second embodiment described above, the dirt detecting units (the dirt detecting units 511 and 521) are provided in the image processing units (the left-eye image processing unit 51A and the right-eye image processing unit 52A), and in detecting the dirt, the control unit 59 is allowed to switch the image signals (the left-eye image signal and the right-eye image signal) to be output to the recording medium 10. According to the second embodiment, at the time of recording one of the image signals for stereoscopic viewing, by suppressing the image in which the dirt is reflected from being recorded on the recording medium 10, it is possible to record an appropriate image signal.

Third Embodiment

Figure 6:
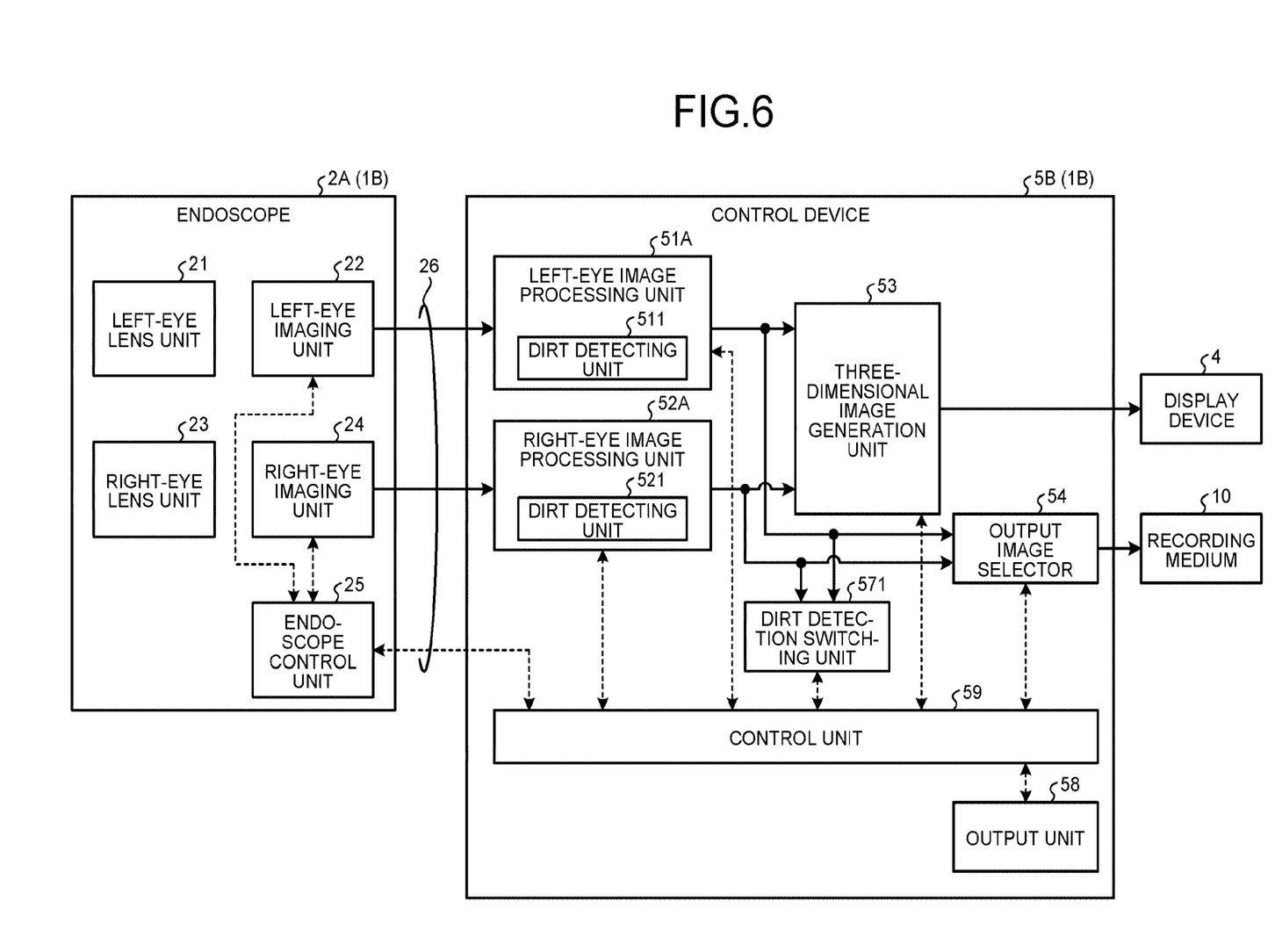
FIG. 6 is a block diagram illustrating configurations of an endoscope and a control device included in an endoscope apparatus according to a third embodiment.

Next, a third embodiment will be described with reference to FIG. 6. FIG. 6 is a block diagram illustrating a configuration of an endoscope 2A and a control device 5B included in an endoscope apparatus 1B according to the third embodiment. In the above-described second embodiment, the rigid endoscope has been described as an example, but in the third embodiment, an endoscope apparatus having a flexible endoscope will be described.

The endoscope apparatus 1B according to the third embodiment includes a flexible endoscope 2A, a display device 4, a light source device 6 (refer to FIG. 1 and the like), and a control device 5B. In the third embodiment, only configurations different from those of the above-described second embodiment will be described. In the endoscope apparatus 1B, the endoscope 2A is directly connected to the control device 5B.

The endoscope 2A has an insertion portion that has flexibility and is introduced into a subject. At the distal end of the insertion portion, a left-eye lens unit 21, a left-eye imaging unit 22, a right-eye lens unit 23, a right-eye imaging unit 24, and an endoscope controller 25 are provided. These configurations of the insertion portion have functions equivalent to the left-eye lens unit 91, the left-eye imaging unit 92, the right-eye lens unit 93 and the right-eye imaging unit 94 described above. The endoscope controller 25 controls the left-eye imaging unit 22 and the right-eye imaging unit 24 under the control of the control unit 59. The image signal generated in the endoscope 2A or the control signal between the endoscope controller 25 and the control unit 59 is transmitted and received via a transmission cable 26.

The endoscope controller 25 is realized by using a general-purpose processor such as a CPU having an internal memory (not illustrated) in which a program is recorded or a dedicated processor such as various arithmetic circuits for executing specific functions such as an ASIC. In addition, this unit may be configured by using an FPGA which is one type of a programmable integrated circuit.

The control device 5B includes a left-eye image processing unit 51A, a right-eye image processing unit 52A, a three-dimensional image generation unit 53, an output image selector 54, an output unit 58, a control unit 59, and a dirt detection switching unit 571. The control device 5B is the same as the above-described control device 5A except that the left-eye detecting unit 55A, the right-eye detecting unit 56A and the detection switching unit 57A as the configuration for performing auto-focus are included.

The flow of processes relating to the selection of the dirt detecting unit and the switching of the output image are the same as the flowchart illustrated in FIG. 4 described above. Each component executes the corresponding process, so that the processes similar to those of the first embodiment are executed. Specifically, when dirt is detected by the dirt detecting unit 511, under the control of the control unit 59, the detecting unit that executes the dirt detection process is switched to the dirt detecting unit 521, and the image signal to be output is also switched.

In the third embodiment described above, in the flexible endoscope 2A, the image processing units (the left-eye image processing unit 51A and the right-eye image processing unit 52A) are provided with dirt detecting units (the dirt detecting units 511 and 521), and when the dirt is detected, the control unit 59 is allowed to switch the image signals (the left-eye image signal and the right-eye image signal) to be output to the recording medium 10. According to the third embodiment, at the time of recording one of the image signals for stereoscopic viewing, by suppressing the image in which the dirt is reflected from being recorded on the recording medium 10, it is possible to record an appropriate image signal.

Fourth Embodiment

Figure 7:
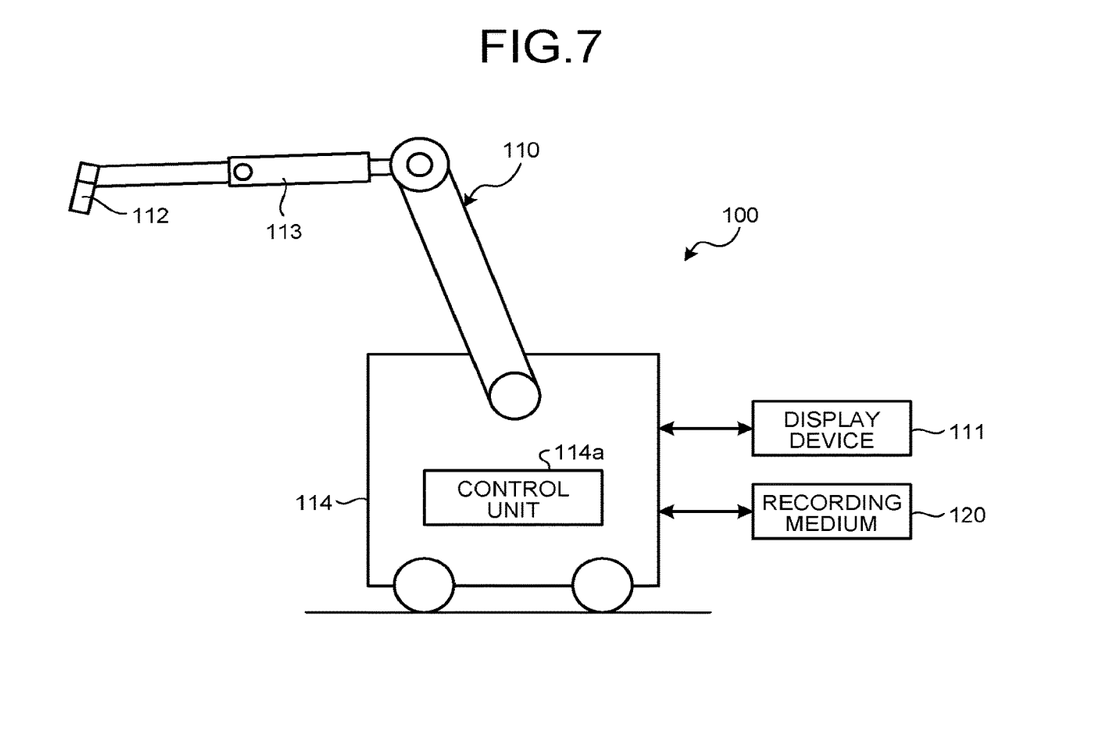
FIG. 7 is a diagram schematically illustrating the overall configuration of a surgical microscope system which is a medical observation system including a medical imaging device according to a fourth embodiment.

Next, a fourth embodiment will be described. FIG. 7 is a diagram schematically illustrating the overall configuration of a surgical microscope system 100 which is a medical observation system including a medical imaging device according to the fourth embodiment. In the first to third embodiments described above, the rigid endoscope or the flexible endoscope has been described as an example. However, in the fourth embodiment, a surgical microscope system (medical image acquisition system) having functions of enlarging and capturing an image of a predetermined field of view area and displaying the captured image will be described as an example.

The surgical microscope system 100 includes a microscope device 110 that is a medical imaging device that acquires an image by capturing the image for observing a subject and a display device 111 that displays the image captured by the microscope device 110. In addition, the display device 111 may be configured to be integrated with the microscope device 110.

The microscope device 110 includes a microscope unit 112 that enlarges and captures an image of a minute portion of a subject, a support unit 113 that is connected to a proximal end portion of the microscope unit 112 and includes an arm rotatably supporting the microscope unit 112, and a base unit 114 that rotatably holds a proximal end portion of the support unit 113 and is movable on the floor surface. The base unit 114 has a control unit 114a for controlling the operation of the surgical microscope system 100. The control unit 114a is provided with, for example, each unit included in the above-described control device 5. In addition, the base unit 114 may be configured not to be movable on the floor surface but to support the support unit 113 by being fixed to a ceiling, a wall surface, or the like. In addition, the base unit 114 may include a light source unit that generates illumination light with which the subject from the microscope device 110 is irradiated.

The microscope unit 112 has, for example, a cylindrical shape and has the configuration of the above-described camera head 9 (or the endoscope 2A) inside thereof. A switch for receiving an input of an operation instruction of the microscope device 110 is provided on the side surface of the microscope unit 112. A cover glass (not illustrated) for protecting the interior is provided on an opening surface of the lower end portion of the microscope unit 112.

In addition, a recording medium 120 is connected to the base unit 114. The recording medium 120 is configured with a removable memory such as a USB memory.

A user such as a surgeon moves the microscope unit 112 and performs an imaging operation while operating various switches in the state where the user grips the microscope unit 112. In addition, it is preferable that the shape of the microscope unit 112 is a shape that is elongated in the observation direction so that the user can grip the microscope unit and change the viewing direction easily. For this reason, the shape of the microscope unit 112 may be a shape other than a columnar shape and may be, for example, a polygonal prism shape.

In the fourth embodiment described above, in the surgical microscope system 100, the dirt detecting units (the dirt detecting units 551 and 561) are provided in the detecting units (the left-eye detecting unit 55 and the right-eye detecting unit 56), and in detecting the dirt, the detection switching unit (the detection switching unit 57) is allowed to switch the image signals (the left-eye image signal and the right-eye image signal) output to the recording medium 120. According to the fourth embodiment, at the time of recording one of the image signals for stereoscopic viewing, by suppressing the image in which the dirt is reflected from being recorded on the recording medium 120, it is possible to record an appropriate image signals.

Up to this point, the mode for carrying out the present disclosure has been described, but the present disclosure is not limited only by the above described first to fourth embodiments. For example, in the first to fourth embodiments described above, it is stated that either one of the dirt detecting units detects dirt, but the two dirt detecting units may be allowed to detect dirt, and the output image selector 54 may select the captured image captured by the imaging unit having a smaller degree of dirt as the captured image to be output to the outside among the detection results of the obtained dirt.

In addition, in the first to fourth embodiments described above, an example where one dirt detecting unit performs dirt detection based on the left-eye image signal, and the other dirt detecting unit performs dirt detection based on the right-eye image signal, that is, an example where two dirt detecting units that perform dirt detection for the respective image signals are provided has been described. However, there may be used a configuration where a dirt detecting unit that shares two dirt detecting units and a selector that selects an image signal of a detection object and outputs the image signal to the dirt detecting unit are included.

As described above, the medical imaging device according to the present disclosure is useful for recording an appropriate image signal at the time of recording one of the image signals for stereoscopic viewing.

According to the present disclosure, it is possible to record an appropriate image signal at the time of recording one of the image signals for stereoscopic viewing.

Although the disclosure has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

What is claimed is:

1. A medical imaging device comprising:
    a first imaging unit configured to capture a first optical image having parallax;
    a second imaging unit configured to capture a second optical image having parallax;
    a first imaging optical system configured to form the first optical image on a light receiving surface of the first imaging unit;
    a second imaging optical system configured to form the second optical image on a light receiving surface of the second imaging unit;
    a dirt detecting unit configured to detect dirt adhered to at least one of the first and the second imaging optical systems by using at least one of a first image signal captured by the first imaging unit and a second image signal captured by the second imaging unit;
    an image generation unit configured to generate a three-dimensional image based on a first captured image based on the first image signal and a second captured image based on the second image signal and cause a display device to display one of the first captured image, the second captured image, and the three-dimensional image; and
    an image selector configured to select a captured image to be output to an outside selected from one of the first captured image and the second captured image based on a detection result of the dirt by the dirt detecting unit.

2. The medical imaging device according to claim 1, wherein the dirt detecting unit includes:
    a first dirt detecting unit configured to detect the dirt adhered to the first imaging optical system by using the first image signal captured by the first imaging unit; and
    a second dirt detecting unit configured to detect the dirt adhered to the second imaging optical system by using the second image signal captured by the second imaging unit.

3. The medical imaging device according to claim 2, further comprising:
    a first detecting unit including the first dirt detecting unit and configured to perform a detection process by using the first image signal captured by the first imaging unit;
    a second detecting unit including the second dirt detecting unit and configured to perform a detection process by using the second image signal captured by the second imaging unit; and
    a detection switching unit configured to:
    set the first detecting unit as a detecting unit that executes detection when no dirt is detected by the first dirt detecting unit; and
    set the second detecting unit as the detecting unit that executes detection when the dirt is detected by the first dirt detecting unit,
    wherein one of the first dirt detecting unit and the second dirt detecting unit executes the dirt detection in accordance with the detecting unit that executes detection, and
    wherein the image selector selects the captured image corresponding to the image signal of a dirt detection target.

4. The medical imaging device according to claim 2, further comprising:
    a first image processing unit including the first dirt detecting unit and configured to generate the first captured image by using the first image signal;
    a second image processing unit including the second dirt detecting unit and configured to generate the second captured image by using the second image signal; and
    a dirt detection switching unit configured to:
    set the first dirt detecting unit as the dirt detecting unit that executes the dirt detection when no dirt is detected by the first dirt detecting unit; and
    set the second dirt detecting unit as the dirt detecting unit that executes the dirt detection when the dirt is detected by the first dirt detecting unit,
    wherein the image selector selects the captured image corresponding to the image signal of a dirt detection target.

5. The medical imaging device according to claim 1, wherein the dirt detecting unit is configured to:

determine whether or not a plurality of detection regions set in the first captured image are in focus on a surface of the first imaging optical system and determine that the dirt adheres when number of detection regions determined as in focus on the surface of the first imaging optical system is larger than a preset threshold value; and determine whether or not a plurality of detection regions set in the second captured image are in focus on a surface of the second imaging optical system and determine that the dirt adheres when number of detection regions determined as in focus on the surface of the second imaging optical system is larger than a preset threshold value.

6. The medical imaging device according to claim 1, wherein the dirt detecting unit detects the dirt adhered to the first and second imaging optical systems by using the first image signal captured by the first imaging unit and the second image signal captured by the second imaging unit, and wherein the image selector selects the captured image captured by the imaging unit having a smaller degree of the dirt among detection results of the dirt by the dirt detecting unit as the captured image to be output to the outside.

7. The medical imaging device according to claim 1, further comprising a notification unit configured to notify that the dirt adheres to at least one of the first and the second imaging optical systems when the dirt is detected in at least one of the first and the second imaging optical systems by the dirt detecting unit.

8. The medical imaging device according to claim 1, further comprising a memory configured to record the captured image selected by the image selector.

9. The medical imaging device according to claim 1, wherein the medical imaging device is connectable to a memory configured to record the captured image selected by the image selector.

10. A medical imaging device comprising:
a first imaging sensor configured to capture a first optical image having parallax;
a second imaging sensor configured to capture a second optical image having parallax;
first imaging optics configured to form the first optical image on a light receiving surface of the first imaging sensor;
second imaging optics configured to form the second optical image on a light receiving surface of the second imaging sensor;
a processor configured to perform as a dirt detecting unit configured to detect dirt adhered to at least one of the first and the second imaging optics by using at least one of a first image signal captured by the first imaging sensor and a second image signal captured by the second imaging sensor;
the processor further configured to perform as an image generation unit configured to generate a three-dimensional image based on a first captured image based on the first image signal and a second captured image based on the second image signal and cause a display device to display one of the first captured image, the second captured image, and the three-dimensional image; and
the processor further configured to perform as an image selector configured to select a captured image to be output to an outside selected from one of the first captured image and the second captured image based on a detection result of the dirt by the dirt detecting unit.

11. The medical imaging device according to claim 10, wherein the dirt detecting unit includes:
a first dirt detecting unit configured to detect the dirt adhered to the first imaging optics by using the first image signal captured by the first imaging sensor; and
a second dirt detecting unit configured to detect the dirt adhered to the second imaging optics by using the second image signal captured by the second imaging sensor.

12. The medical imaging device according to claim 11, wherein the processor is further configured to perform as:
a first detecting unit including the first dirt detecting unit and configured to perform a detection process by using the first image signal captured by the first imaging sensor;
a second detecting unit including the second dirt detecting unit and configured to perform a detection process by using the second image signal captured by the second imaging sensor; and
a detection switching unit configured to:
set the first detecting unit as a detecting unit that executes detection when no dirt is detected by the first dirt detecting unit; and
set the second detecting unit as the detecting unit that executes detection when the dirt is detected by the first dirt detecting unit,
wherein one of the first dirt detecting unit and the second dirt detecting unit executes the dirt detection in accordance with the detecting unit that executes detection, and
wherein the image selector selects the captured image corresponding to the image signal of a dirt detection target.

13. The medical imaging device according to claim 11, wherein the processor is further configured to perform as:
a first image processing unit including the first dirt detecting unit and configured to generate the first captured image by using the first image signal;
a second image processing unit including the second dirt detecting unit and configured to generate the second captured image by using the second image signal; and
a dirt detection switching unit configured to:
set the first dirt detecting unit as the dirt detecting unit that executes the dirt detection when no dirt is detected by the first dirt detecting unit; and
set the second dirt detecting unit as the dirt detecting unit that executes the dirt detection when the dirt is detected by the first dirt detecting unit,
wherein the image selector selects the captured image corresponding to the image signal of a dirt detection target.

14. The medical imaging device according to claim 10, wherein the dirt detecting unit is configured to:
determine whether or not a plurality of detection regions set in the first captured image are in focus on a surface of the first imaging optics and determine that the dirt adheres when number of detection regions determined as in focus on the surface of the first imaging optics is larger than a preset threshold value; and
determine whether or not a plurality of detection regions set in the second captured image are in focus on a surface of the second imaging optics and determine that the dirt adheres when number of detection regions determined as in focus on the surface of the second imaging optics is larger than a preset threshold value.

15. The medical imaging device according to claim 10, wherein the dirt detecting unit detects the dirt adhered to the first and second imaging optics by using the first image signal captured by the first imaging sensor and the second image signal captured by the second imaging sensor, and wherein the image selector selects the captured image captured by the imaging unit having a smaller degree of the dirt among detection results of the dirt by the dirt detecting unit as the captured image to be output to the outside.

16. The medical imaging device according to claim 10, wherein the processor if further configured to perform as a notification unit configured to notify that the dirt adheres to at least one of the first and the second imaging optics when the dirt is detected in at least one of the first and the second imaging optics by the dirt detecting unit.

17. The medical imaging device according to claim 10, further comprising a memory configured to record the captured image selected by the image selector.

18. The medical imaging device according to claim 10, wherein the medical imaging device is connectable to a memory configured to record the captured image selected by the image selector.

\* \* \* \* \*